(12) United States Patent
Valentine et al.

(10) Patent No.: US 11,357,508 B2
(45) Date of Patent: Jun. 14, 2022

(54) ILLUMINATED TROCAR ASSEMBLY FOR SURGICAL STAPLING INSTRUMENT

(71) Applicant: Covidien LP, Mansfield, MA (US)

(72) Inventors: David E. Valentine, Hamden, CT (US); Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 147 days.

(21) Appl. No.: 16/866,841

(22) Filed: May 5, 2020

(65) Prior Publication Data

US 2021/0346026 A1    Nov. 11, 2021

(51) Int. Cl.
| | | |
|---|---|---|
| *A61B 17/115* | (2006.01) | |
| *A61B 90/30* | (2016.01) | |
| *A61B 17/00* | (2006.01) | |
| *A61B 17/072* | (2006.01) | |

(52) U.S. Cl.
CPC .......... *A61B 17/1155* (2013.01); *A61B 90/30* (2016.02); *A61B 2017/00398* (2013.01); *A61B 2017/00486* (2013.01); *A61B 2017/07257* (2013.01); *A61B 2017/07271* (2013.01); *A61B 2090/309* (2016.02)

(58) Field of Classification Search
CPC ............................ A61B 17/1155; A61B 90/30
See application file for complete search history.

(56) References Cited

U.S. PATENT DOCUMENTS

| | | | | |
|---|---|---|---|---|
| 5,309,927 A | * | 5/1994 | Welch | A61B 17/0218 128/898 |
| 6,338,737 B1 | * | 1/2002 | Toledano | A61B 17/115 227/175.1 |
| 7,303,106 B2 | | 12/2007 | Milliman et al. | |
| 8,801,735 B2 | | 8/2014 | Shelton, IV et al. | |
| 9,010,605 B2 | | 4/2015 | Olson et al. | |
| 9,757,133 B2 | * | 9/2017 | Latimer | A61B 17/105 |
| 10,080,566 B2 | | 9/2018 | Milliman | |
| 2014/0326777 A1 | | 11/2014 | Zingman | |

(Continued)

FOREIGN PATENT DOCUMENTS

ES    2550808 T3    11/2015

OTHER PUBLICATIONS

Extended European Search Report issued in corresponding European Application No. 21172057.8 dated Oct. 6, 2021, 9 pages.

*Primary Examiner* — Nathaniel C Chukwurah
(74) *Attorney, Agent, or Firm* — Carter, Deluca & Farrell LLP

(57) ABSTRACT

A surgical stapling instrument includes an anvil assembly, a shell assembly, and an adapter assembly. The adapter assembly includes a tubular shaft supporting the shell assembly at a distal portion of the tubular shaft, and a trocar assembly transitionable between an extended configuration and a retracted configuration. The trocar assembly includes a trocar detachably supporting the anvil assembly thereon, a lead screw adapted to be coupled to an actuator for rotational input, a first member rotatably supporting the lead screw, a second member operatively coupled to the lead screw such that rotation of the lead screw causes axial displacement of the second member relative to the first member, and a light diffuser configured to scatter light received from a light source. The light diffuser is configured to be surrounded by the anvil center rod when the anvil center rod is attached to the trocar.

20 Claims, 5 Drawing Sheets

(56) References Cited

U.S. PATENT DOCUMENTS

| | | |
|---|---|---|
| 2019/0343517 A1 | 11/2019 | Zemlok et al. |
| 2019/0380714 A1 | 12/2019 | Chen et al. |
| 2020/0015820 A1 | 1/2020 | Contini et al. |

* cited by examiner

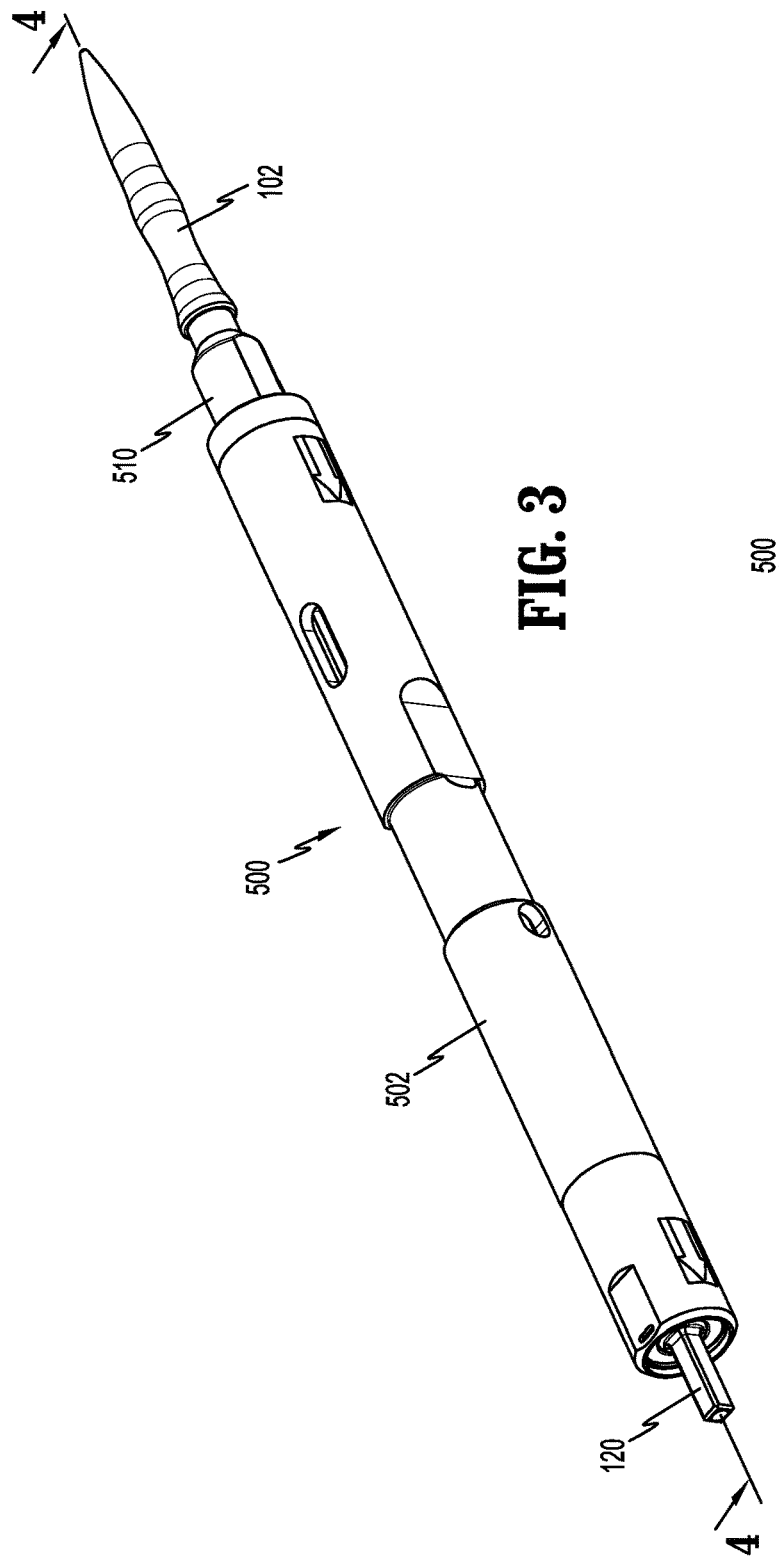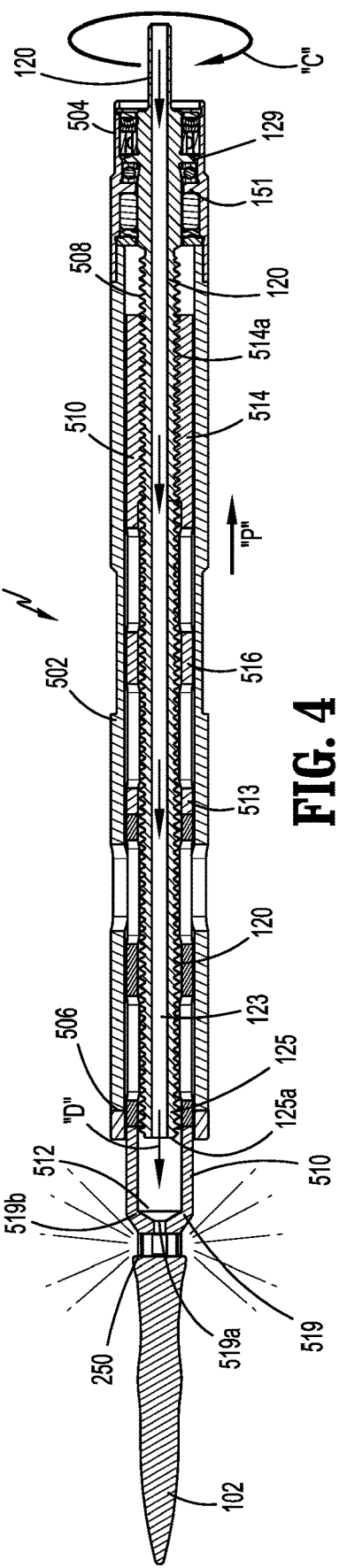

ILLUMINATED TROCAR ASSEMBLY FOR SURGICAL STAPLING INSTRUMENT

FIELD

The disclosure relates generally to surgical stapling instruments, and more particularly, to an illuminated trocar assembly for surgical stapling instruments.

BACKGROUND

Anastomosis is the surgical joining of separate hollow organ sections. Typically, an anastomosis procedure follows surgery in which a diseased or defective section of hollow tissue is removed, and the end sections are stapled via a surgical stapling instrument. Depending on the desired anastomosis procedure, the end sections may be joined by circular or side-to-side organ reconstruction methods, for instance.

In a circular anastomosis procedure, the two ends of the organ sections are joined by means of a surgical stapling instrument which drives a circular array of staples through the end section of each organ section and simultaneously cores any tissue interior of the driven circular array of staples to free the tubular passage. Typically, these surgical stapling instruments include an elongated body portion having a handle portion at a proximal end to actuate the surgical stapling instrument and a staple holding component disposed at a distal end. An anvil assembly including an anvil retention rod with an attached anvil head is mounted to a trocar assembly at the distal end of the surgical stapling instrument adjacent the staple-holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are formed by the anvil head. An annular knife is advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a surgical stapling instrument for hemorrhoid treatment, the anvil head and the staple holding-component of the surgical stapling instrument are inserted through the anus and into the rectum with the anvil head and the staple-holding component in an open or spaced part position. Thereafter, a purse string suture is used to pull the internal hemorrhoidal tissue towards the anvil rod. Next, the anvil head and staple-holding component are approximated to clamp the hemorrhoidal tissue between the anvil head and the staple holding component. During the approximation of the anvil head and the staple-holding component, the trocar assembly is engaged with the anvil retention rod. The surgical stapling instrument is fired to remove the hemorrhoidal tissue and staple the tissue.

SUMMARY

In accordance with the disclosure, a surgical stapling instrument includes an anvil assembly, a shell assembly, and an adapter assembly. The anvil assembly includes an anvil head and an anvil center rod extending proximally from the anvil head. The shell assembly includes an annular cartridge adapted to house a plurality of staples. The adapter assembly includes a tubular shaft supporting the shell assembly at a distal portion of the tubular shaft, and a trocar assembly. The trocar assembly includes a trocar detachably supporting the anvil center rod thereon and a light diffuser configured to scatter light received from a light source. The light diffuser is disposed adjacent a proximal portion of the trocar such that the light diffuser is surrounded by the anvil center rod when the anvil center rod is attached to the trocar.

In an aspect, the trocar assembly may further include a first member, a second member supporting the trocar at a distal end portion of the second member, and a lead screw adapted to be coupled to an actuator for rotational input. The lead screw may be rotatably supported on the first member and operatively coupled to the second member such that rotation of the lead screw causes axial displacement of the second member relative to the first member.

In another aspect, the second member may include an engaging portion defining a threaded bore threadably engaged with the lead screw.

In yet another aspect, the second member may further include a receiving portion distal of the engaging portion. The receiving portion may define a longitudinal channel configured to receive the lead screw.

In an aspect, the distal end portion of the second member may be tapered.

In another aspect, the distal end portion of the second member may include a neck portion configured to support the light diffuser about the neck portion. The neck portion may have a diameter smaller than a diameter of the trocar.

In yet another aspect, the distal end portion of the second member may define a bore in communication with the light diffuser.

In still yet another aspect, the trocar and the second member may be integrally formed or monolithically formed.

In still yet another aspect, the lead screw may define a second longitudinal channel extending therethrough.

In an aspect, the lead screw may include a distal end portion defining an opening such that the second longitudinal channel is in communication with the light diffuser.

In another aspect, the lead screw may include an annular protrusion configured to be received in a circular groove defined in an inner surface of the first member to inhibit axial displacement of the lead screw during rotation thereof.

In yet another aspect, the first member of the trocar assembly may be axially fixed with the tubular shaft.

In accordance with another aspect of the disclosure, an adapter assembly for use with a surgical stapling instrument includes a light source, a tubular shaft supporting a shell assembly of the surgical stapling instrument at a distal portion of the tubular shaft, and a trocar assembly attachable to an anvil assembly of the surgical stapling instrument. The trocar assembly is transitionable between an extended configuration and a retracted configuration. The trocar assembly includes a trocar detachably supporting the anvil center rod thereon, a lead screw adapted to be coupled to an actuator for rotational input, a first member rotatably supporting the lead screw, a second member operatively coupled to the lead screw such that rotation of the lead screw causes axial displacement of the second member relative to the first member, and a light diffuser. The lead screw defines a pathway of the light transmitted by the light source. The light diffuser is in communication with the pathway of the lead screw. The light diffuser is mounted about the second member and configured to be surrounded by the anvil center rod when the anvil center rod is attached to the trocar.

In an aspect, the trocar and the second member may be formed as a single construct.

In another aspect, the first member may be dimensioned to receive the second member therein.

In yet another aspect, the light source may be an LED.

In still yet another aspect, the second member may include an engaging portion defining a threaded bore threadably engageable with the lead screw, and a receiving portion defining a channel in communication with the light diffuser.

In still yet another aspect, the second member and the lead screw may be concentrically arranged.

In still yet another aspect, a portion of the channel of the receiving portion of the second member may be tapered.

In still yet another aspect, the light source may be disposed proximal of the lead screw.

BRIEF DESCRIPTION OF DRAWINGS

A trocar assembly for use with a surgical stapling instrument is disclosed herein with reference to the drawings, wherein:

FIG. 3 is a perspective view of a trocar assembly of the surgical stapling instrument of FIG. 1;

FIG. 4 is a cross-sectional view of the trocar assembly of FIG. 3 taken along section line 4-4 of FIG. 3;

DETAILED DESCRIPTION

Figure 1:
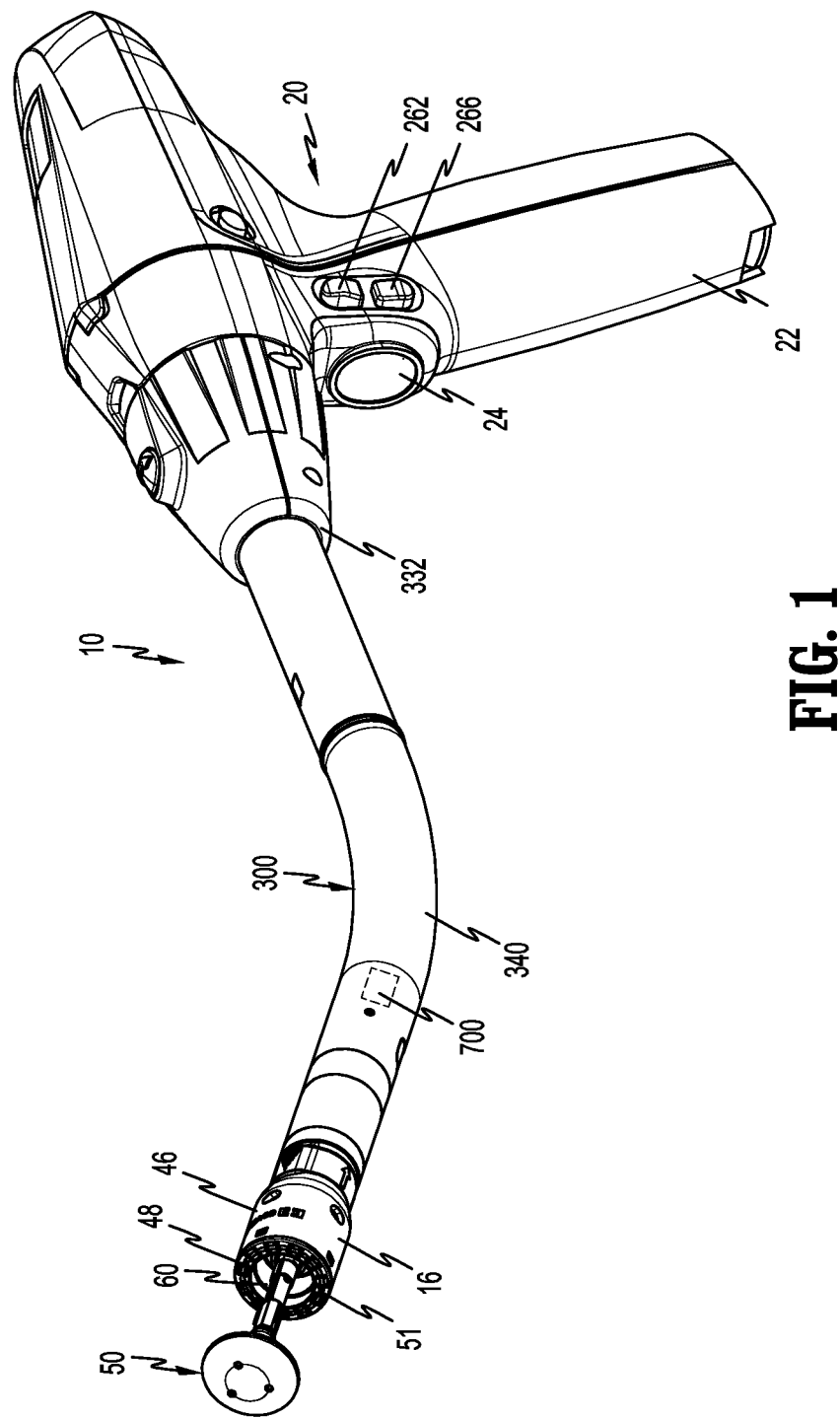
FIG. 1 is a perspective view of a surgical stapling instrument in accordance with the disclosure.

A surgical stapling instrument is described in detail with reference to the drawings, wherein like reference numerals designate corresponding elements in each of the several views. As used herein, the term "distal" refers to that portion of the instrument, or component thereof which is farther from the user during customary use of the instrument while the term "proximal" refers to that portion of the instrument or component thereof which is closer to the user during customary use of the instrument.

Figure 2:
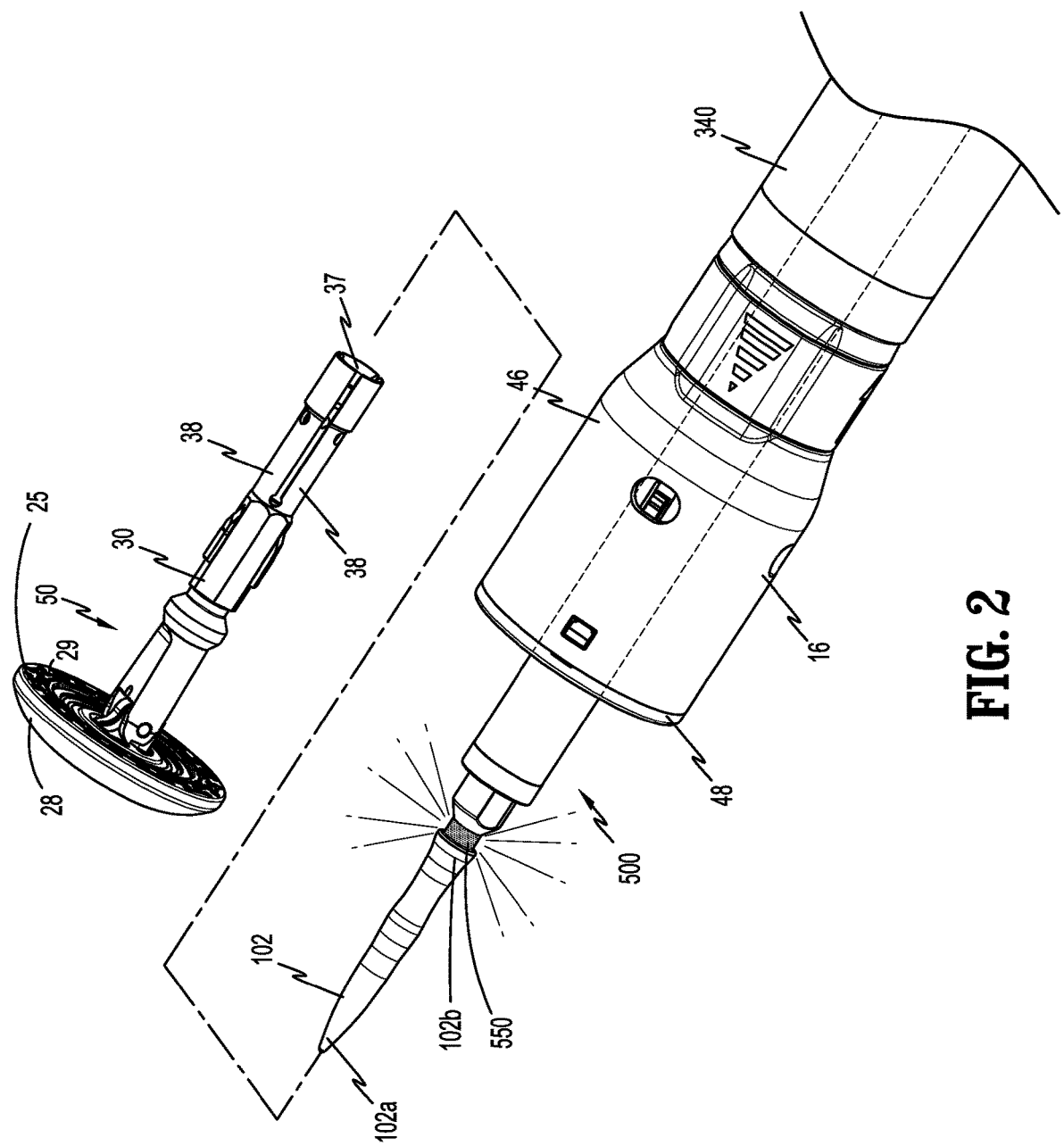
FIG. 2 is a perspective view of an anvil assembly and a shell assembly of the surgical stapling instrument of FIG. 1.

With reference to FIGS. 1 and 2, a trocar assembly for use with a surgical instrument, in the form of a surgical stapling instrument 10 is shown generally as 500. The trocar assembly 500 includes a light-emitting band (shown as a light diffuser 250) that assists the clinician during attachment of an anvil assembly 50 to the trocar assembly 500, as will be discussed. The light-emitting band further assists the clinician in determining whether the anvil assembly 50 is properly attached to the trocar assembly 50. The surgical stapling instrument 10 is a circular stapling instrument including a handle assembly 20, an adapter assembly 300 extending distally from the handle assembly 20 and including the trocar assembly 500 in accordance with the disclosure, a shell assembly 16 supported on a distal portion of the adapter assembly 300, and an anvil assembly 50 operatively coupled to the handle assembly 20.

The handle assembly 20 is illustrated as a powered assembly and includes a stationary grip 22, an actuation button 24 for controlling firing of staples (not shown) from an annular staple cartridge 48 of the shell assembly 16, and approximation buttons 26a, 26b for controlling axial displacement of the anvil assembly 50 towards and away from the shell assembly 16. For a detailed description of the structure and function of exemplary powered handle assemblies, reference may be made to U.S. Patent Application Publication Nos. 2020/0015820 and 2019/0343517, the entire contents of which are incorporated herein by reference. Although the disclosure illustrates a powered assembly, it is envisioned that the advantages of the present disclosure as described in detail below are also applicable to surgical stapling instruments having manually operated handle and body assemblies or robotically actuated surgical instruments. U.S. Pat. No. 7,303,106 (the '106 patent) discloses an example of a surgical stapling instrument including a manually actuated handle assembly and is incorporated herein by reference in its entirety. It is also envisioned that the disclosed stapling instrument can be supported on a robotic system and need not include a handle assembly.

With continued reference to FIGS. 1 and 2, the adapter assembly 300 includes an interface portion 332 detachably coupled to the handle assembly 20, a tubular shaft 340 extending distally from the interface portion 332, and the trocar assembly 500 operatively supported within the tubular shaft 340. The shell assembly 16 is supported on a distal portion of the tubular shaft 340 and includes a shell housing 46 and an annular staple cartridge 48 that defines annular rows of staple receiving pockets 51. In particular, the shell assembly 16 may be releasably coupled to the distal portion of the tubular shaft 340 to facilitate replacement of the annular staple cartridge 48 after each use.

Each of the staple receiving pockets 51 supports a staple (not shown) that can be fired from the annular staple cartridge 48 via actuation of the actuation button 24 of the handle assembly 20 and formed within the staple forming pockets 25 of a staple forming surface 29 of an anvil head 28 of the anvil assembly 50. The shell housing 46 of the shell assembly 16 defines an annular cavity 60. The annular cavity 60 supports a staple pusher (not shown) and an annular knife (not shown) such that the staple pusher and the annular knife are movable in relation to the annular staple cartridge 48 to eject the staples from the annular staple cartridge 48 and to dissect or cut tissue positioned within an annulus defined by the annular staple cartridge 48. For a detailed description of the structure and function of the exemplary shell assemblies reference may be made to the '106 patent.

With particular reference to FIG. 2, the anvil assembly 50 includes an anvil head 28 and an anvil center rod 30. The anvil head 28 includes the staple forming surface 29 that includes staple forming pockets 25. The anvil center rod 30 includes a plurality of resilient fingers 38 defining a longitudinal bore 37 that is dimensioned to receive and releasably engage a trocar 102 of the trocar assembly 500. In an aspect, the anvil head 28 may be pivotally coupled to the anvil center rod 30 and may be movable between an operative position for forming staples and a tilted, reduced profile position. The anvil assembly 50 may be releasably coupled to the trocar assembly 500 for concomitant axial displacement therewith relative to the shell assembly 16 (FIG. 1) by activating an actuator (not shown) such as, e.g., an electric motor, in the handle assembly 20 (FIG. 1). The trocar 102 includes a distal portion 102a that is tapered and a proximal portion 102b has a diameter larger than a diameter of the distal portion 102a. The distal portion 102a is detachably received within the longitudinal bore 37 that is defined by the plurality resilient fingers 38 of the anvil assembly 50. Rotational input to the trocar assembly 500 (FIG. 3) transitions the anvil assembly 50 between a spaced apart configuration and an approximated configuration, in which, the staple forming surface 29 of the anvil assembly 50 is in juxtaposed alignment with the annular staple cartridge 48.

With reference now to FIGS. 3 and 4, the trocar assembly 500 includes an outer member 502, an inner member 510 slidably disposed within the outer member 502, a lead screws 120, and the trocar 102. In particular, the outer member 502, the inner member 510, the lead screw 120, and the trocar 102 may be concentrically arranged. The outer member 502 includes proximal and distal end portions 504, 506 and defines a first longitudinal channel 508 therein. In particular, the lead screw 120 is rotatably supported on, e.g., the proximal end portion 504, of the outer member 502. The lead screw 120 includes an annular protrusion 129 configured to be received in a circular groove defined in an inner surface of the outer member 502 to inhibit axial displacement of the lead screw 120 during rotation of the lead screw 120. The outer member 502 may include a circular protrusion 151 extending radially inward from an inner surface thereof. The circular protrusion 151 is configured to rotatably support the lead screw 120 thereon. The lead screw 120 is operatively coupled to an actuator (not shown) such as, e.g., an electric motor, in the handle assembly 20 (FIG. 1) for rotational input. For example, a cable (not shown) may interconnect the lead screw 120 and the actuator for rotational input. The cable may be formed of a flexible material to enable flexion of the cable in, e.g., radial and/or axial, directions. In this manner, the cable may accommodate the shape and contour of the adapter assembly 300. Rotation of the lead screw 120 causes axial displacement of the anvil assembly 50 as will be described.

With particular reference to FIG. 4, the distal end portion 506 of the outer member 502 defines an opening dimensioned to receive the inner member 510 therethrough to enable relative axial displacement of the inner member 510 within the first longitudinal channel 508 of the outer member 502. The inner member 510 includes a tubular body 513 including an engaging portion 514 and a receiving portion 516 distal of the engaging portion 514. The engaging portion 514 defines a threaded bore 514a that threadably engages the lead screw 120. The receiving portion 516 is configured to support the trocar 102 at a distal end portion 519 of the receiving portion 516. The inner member 510 and the trocar 102 may be integrally formed as a single construct. Alternatively, the inner member 510 and the trocar 102 may be monolithically formed. However, it is contemplated that the trocar 102 may be detachably supported at the distal end portion 519 of the receiving portion 516. The receiving portion 516 of the inner member 510 defines a second longitudinal channel 512 extending along a length thereof. The second longitudinal channel 512 is dimensioned to receive the lead screw 120 therein. The lead screw 120 defines a third longitudinal channel 123 along the length thereof. In addition, the lead screw 120 further defines an opening 125a at a distal end portion 125 of the lead screw 120 such that the third longitudinal channel 123 is in communication with the second longitudinal channel 512 of the receiving portion 516 of the inner member 510. The distal end portion 519 of the inner member 510 includes a light diffuser 250 that serves to diffuse light emitted through the second longitudinal channel 512 of the inner member 510.

When the lead screw 120 engages the threaded bore 514a of engaging portion 514 of the inner member 510 and rotated in the direction of, e.g., an arrow "C", by activation of the actuator in the handle assembly 20, the inner member 510 is axially displaced in the direction of an arrow "P". Axial displacement of the inner member 510 imparts concomitant axial displacement to the trocar 102. Rotation of the lead screw 120 in the direction opposite of the arrow "C" causes axial displacement of the inner member 510 and the trocar 102 in the direction opposite of the arrow "P".

With particular reference to FIG. 4, the adapter assembly 300 includes a light source 700 (FIG. 1) such as, e.g., a light emitting diode (LED), that emits light through the third longitudinal channel 123 of the lead screw 120. In this manner, the third longitudinal channel 123 serves as a pathway of the light emitted by the light source 700. The third longitudinal channel 123 may include a surface or a coating that directs the light towards the distal end portion 125 of the lead screw 120. Alternatively, the third longitudinal channel 123 may include a fiber-optic cable to transmit light therethrough. The distal end portion 519 of the receiving portion 516 of the inner member 510 may be tapered to direct the light towards the light diffuser 250. In particular, the distal end portion 519 defines an opening 519a that provides communication between the light diffuser 250 and the third longitudinal channel 123 of the lead screw 120. The light diffuser 250 is circumferentially mounted about a neck portion extending from the tapered portion 519b of the inner member 510. Under such a configuration, when the light source 700 transmits light through the pathway provided by the third longitudinal channel 123 of the lead screw 120, the light reaches the second longitudinal channel 512 of the inner member 510 and ultimately reaches the light diffuser 250 through the opening 519a. The light diffuser 250 circumferentially scatters the light to be detected by the clinician. In this manner, the light scattered by the light diffuser 250 may assist the clinician to locate and attach the anvil assembly 50 to the trocar 102.

Figure 5:
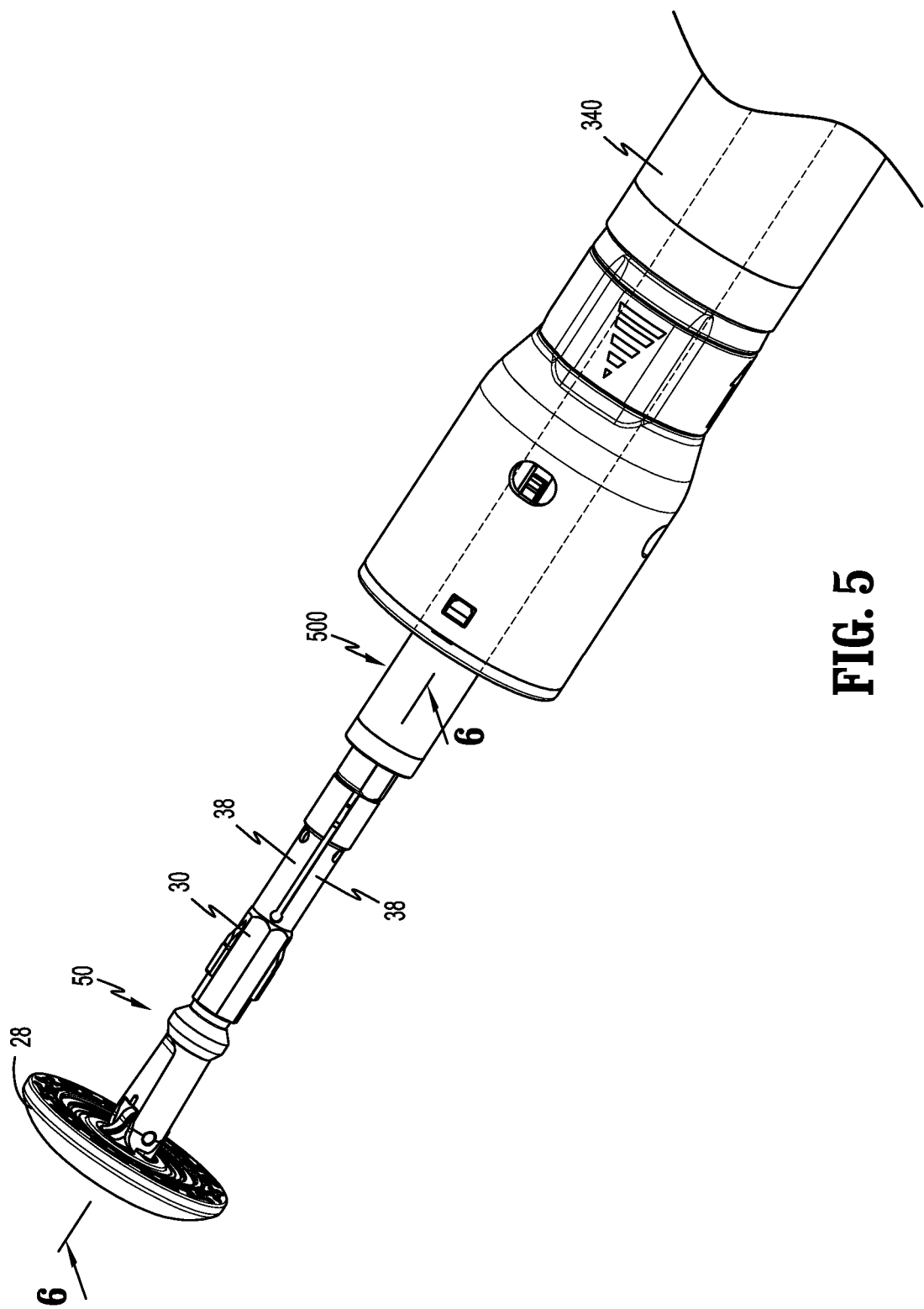
FIG. 5 is a perspective view of the anvil assembly and the shell assembly of FIG. 2, illustrating attachment of the anvil assembly to the trocar assembly.
Figure 6:
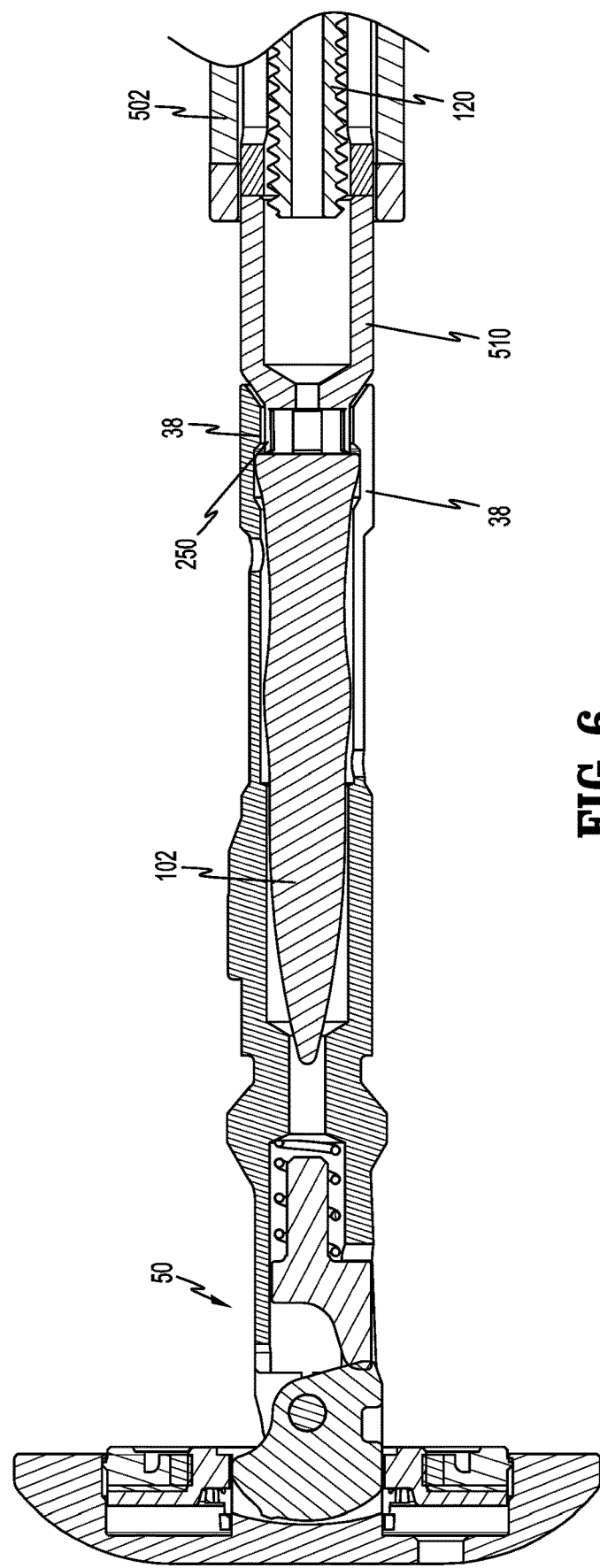
FIG. 6 is a cross-sectional view of the anvil assembly and the shell assembly of FIG. 5 taken along section line 6-6 of FIG. 5.

With reference to FIGS. 5 and 6, when the anvil assembly 50 is properly attached to the trocar assembly 500, the light diffuser 250 on the inner member 510 is surrounded by the plurality of resilient fingers 38 of the anvil assembly 50. In this manner, the presence or absence of the light emitted by the light diffuser 250 may indicate to the clinician whether the anvil assembly 50 is properly attached to the trocar 102.

Initially, a first segment of a tubular tissue may be secured to the anvil assembly 50, and a second segment of a tubular tissue may be secured to the trocar assembly 500, by, e.g., purse string suture. At this time, the light source 700 of the adapter assembly 300 emits light to the light diffuser 250 through the third longitudinal channel 123 of the lead screw 120 and the second longitudinal channel 512 of the inner member 510. The light scattered by the light diffuser 250 is detected by the clinician and assists the clinician in attaching the anvil assembly 50 to the trocar 102. Presence or absence of light scattered by the light diffuser 250 may indicate to the clinician whether or not the anvil assembly 50 is properly attached to the trocar 102. The first and second sections of the tubular tissue are placed between the anvil head 28 and the shell assembly 16 to perform anastomosis. At this time, the surgical stapling instrument 10 may be in the spaced apart configuration (FIG. 1). The approximation button 26a may be pressed to transition the anvil head 28 of the anvil assembly 50 to the approximated configuration to clamp tissue between the anvil head 28 and the annular cartridge assembly 48. At this time, the actuator of the handle assembly is activated to provide rotational input to the lead screw 120. Rotation of the lead screw 120 provides axial displacement of the inner member 510 in the direction of the arrow "P" (FIG. 4), which, in turn, retracts the anvil head 28 to the approximated configuration. At this time, tissue is clamped between the anvil head 28 and the shell assembly 16. Thereafter, the actuation button 24 may be pressed to activate an actuator to perform stapling and cutting of tissue disposed between the anvil head 28 and the shell assembly 16. Thereafter, the clinician may press the approximation button 26*b* to transition the anvil head 28 to the spaced apart configuration. After the surgical procedure, the anvil assembly 50 may be detached from the trocar 102 and the adapter assembly 300 and the anvil assembly 50 may be reprocessed or sterilized for reuse.

Persons skilled in the art will understand that the instruments and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical stapling instrument comprising:
   an anvil assembly including an anvil head and an anvil center rod extending proximally from the anvil head;
   a shell assembly including an annular cartridge adapted to house a plurality of staples; and
   an adapter assembly including:
      a tubular shaft supporting the shell assembly at a distal portion of the tubular shaft; and
      a trocar assembly including:
         a trocar detachably supporting the anvil center rod thereon;
         a first member;
         a second member supporting the trocar at a distal end portion of the second member;
         a lead screw adapted to be coupled to an actuator for rotational input, the lead screw rotatably supported on the first member and operatively coupled to the second member such that rotation of the lead screw causes axial displacement of the second member relative to the first member; and
         a light diffuser configured to scatter light received from a light source, the light diffuser disposed adjacent a proximal portion of the trocar such that the light diffuser is surrounded by the anvil center rod when the anvil center rod is attached to the trocar.

2. The surgical stapling instrument according to claim 1, wherein the second member includes an engaging portion defining a threaded bore threadably engaged with the lead screw.

3. The surgical stapling instrument according to claim 2, wherein the second member further includes a receiving portion distal of the engaging portion, the receiving portion defining a longitudinal channel configured to receive the lead screw.

4. The surgical stapling instrument according to claim 1, wherein the distal end portion of the second member is tapered.

5. The surgical stapling instrument according to claim 1, wherein the distal end portion of the second member includes a neck portion configured to support the light diffuser about the neck portion, the neck portion having a diameter smaller than a diameter of the trocar.

6. The surgical stapling instrument according to claim 1, wherein the distal end portion of the second member defines a bore in communication with the light diffuser.

7. The surgical stapling instrument according to claim 1, wherein the trocar and the second member are integrally formed or monolithically formed.

8. The surgical stapling instrument according to claim 1, wherein the lead screw defines a second longitudinal channel extending therethrough.

9. The surgical stapling instrument according to claim 8, wherein the lead screw includes a distal end portion defining an opening such that the second longitudinal channel is in communication with the light diffuser.

10. The surgical stapling instrument according to claim 1, wherein the lead screw includes an annular protrusion configured to be received in a circular groove defined in an inner surface of the first member to inhibit axial displacement of the lead screw during rotation thereof.

11. The surgical stapling instrument according to claim 1, wherein the first member of the trocar assembly is axially fixed with the tubular shaft.

12. An adapter assembly for use with a surgical stapling instrument comprising:
   a light source;
   a tubular shaft supporting a shell assembly of the surgical stapling instrument at a distal portion of the tubular shaft; and
   a trocar assembly attachable to an anvil assembly of the surgical stapling instrument, the trocar assembly transitionable between an extended configuration and a retracted configuration, the trocar assembly including:
      a trocar detachably supporting the anvil center rod thereon;
      a lead screw adapted to be coupled to an actuator for rotational input, the lead screw defining a pathway of the light transmitted by the light source;
      a first member rotatably supporting the lead screw;
      a second member operatively coupled to the lead screw such that rotation of the lead screw causes axial displacement of the second member relative to the first member; and
      a light diffuser in communication with the pathway of the lead screw, the light diffuser mounted about the second member and configured to be surrounded by the anvil center rod when the anvil center rod is attached to the trocar.

13. The adapter according to claim 12, wherein the trocar and the second member are formed as a single construct.

14. The adapter according to claim 12, wherein the first member is dimensioned to receive the second member therein.

15. The adapter according to claim 12, wherein the light source is an LED.

16. The adapter according to claim 12, wherein the second member includes an engaging portion defining a threaded bore threadably engageable with the lead screw, and a receiving portion defining a channel in communication with the light diffuser.

17. The adapter according to claim 16, wherein a portion of the channel of the receiving portion of the second member is tapered.

18. The adapter according to claim 12, wherein the second member and the lead screw are concentrically arranged.

19. The adapter according to claim 12, wherein the light source is disposed proximal of the lead screw.

20. A surgical stapling instrument comprising:
   an anvil assembly including an anvil head and an anvil center rod extending proximally from the anvil head;
   a shell assembly including an annular cartridge adapted to house a plurality of staples; and
   an adapter assembly including:
      a tubular shaft supporting the shell assembly at a distal portion of the tubular shaft; and a trocar assembly including:
- a trocar detachably supporting the anvil center rod thereon;
- a first member axially fixed with the tubular shaft;
- a second member supporting the trocar at a distal end portion of the second member and movable relative to the first member; and
- a light diffuser disposed adjacent a proximal portion of the trocar such that the light diffuser is obstructed by the anvil center rod when the anvil center rod is attached to the trocar.

* * * * *